United States Patent [19]

Krouwer et al.

[11] Patent Number: 4,575,488

[45] Date of Patent: Mar. 11, 1986

[54] INTERFERENCE FREE TRANSAMINASE ASSAY

[75] Inventors: Jan S. Krouwer, Valhalla; Michael J. Lynch, New Rochelle, both of N.Y.

[73] Assignee: Technicon Instruments Corp., Tarrytown, N.Y.

[21] Appl. No.: 392,038

[22] Filed: Jun. 25, 1982

[51] Int. Cl.$^4$ ............................ C12Q 1/52; C12Q 1/32
[52] U.S. Cl. ...................................... 435/16; 435/26; 435/810
[58] Field of Search ................... 435/16, 26, 174, 180, 435/184, 190, 193, 810

[56] References Cited

U.S. PATENT DOCUMENTS

| | | | |
|---|---|---|---|
| 3,458,403 | 7/1969 | Katsunuma | 435/16 |
| 4,235,962 | 11/1980 | Sanderson | 435/16 |
| 4,241,179 | 12/1980 | Madappally et al. | 435/16 |
| 4,271,265 | 6/1981 | Deneke et al. | 435/16 |
| 4,372,874 | 2/1983 | Modrovich | 435/16 |
| 4,450,232 | 5/1984 | Sanford et al. | 435/16 |

FOREIGN PATENT DOCUMENTS 56-8691  1/1981  Japan ................................. 435/180

OTHER PUBLICATIONS

Sanderson, Clin. Chem., 27(6):1035, Abst. 054 (1981).
Bergmeyer et al., Clin. Chem. 24(4):720–721, (1978).
Bergmeyer et al., Clin. Chem., 23(5):887–893, (1977).

Primary Examiner—Esther M. Kepplinger
Attorney, Agent, or Firm—James R. Cartiglia

[57] ABSTRACT

Compositions for pyridoxal-5'-phosphate (PLP) activated transaminase determinations are provided, in which interference due to PLP is avoided. Amino-functionalized polymers bind PLP which is not associated with the apotransaminase in the sample to be tested, thereby avoiding signal interference, e.g. background absorbance, due to PLP.

15 Claims, 2 Drawing Figures

INTERFERENCE FREE TRANSAMINASE ASSAY

BACKGROUND OF THE INVENTION

1. Field of the Invention

The present invention relates to the field of pyridoxal-5'-phosphate (PLP) activated assays for transaminases such as glutamate oxalacetate transaminase (GOT) and glutamate pyruvate transaminase (GPT).

2. Brief Description of the Prior Art

Transamination is the transfer of an amino group from one molecule to another without the intermediate formation of ammonia. Enzymes that catalyze transaminations are referred to as aminotransferases or, more commonly, transaminases. The two substrate-specific transaminases which have been described in serum are glutamate oxalacetate transaminase (GOT) and glutamate pyruvate transaminase (GPT). The mentioned transaminases catalyze the following reactions:

(a) GOT

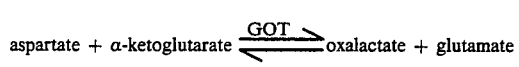
(1)

(b) GPT

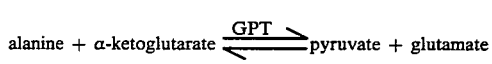
(2)

The most important uses for serum measurements of GOT and GPT are in myocardial infarction and hepatobiliary disease. The methods normally used in the clinical laboratory to measure GOT and GPT involve kinetic, NADH-coupled (NADH is reduced nicotine adenine dinucleotide) reactions monitored at 340 nanometers (nm). These coupled reactions use malate dehydrogenase (MDH) and lactate dehydrogenase (LDH), respectively, and are as follows:

(a) GOT

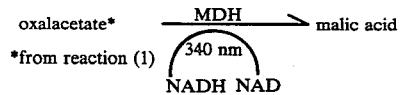
(3)

(b) GPT

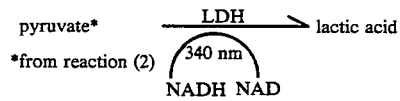
(4)

The method for GOT was introduced by LaDue et al in Science, *Serum Oxalacetic Transaminase Activity in Human Acute Transmural Myocardial Infarction,* 120:497 (1954). The method for GPT was described by Henley et al in J. Lab. Clin. Med., *A New Method for the Determination of Glutamic Oxalacetate and Glutamic Pyruvic Transaminase in Plasma,* 46:785 (1955). Alternatively, the glutamate from reaction (1) or (2) can be reacted with NAD in the presence of glutamate dehydrogenase to produce NADH, which can be measured. With various modifications and improvements, these are still the methods of choice for the measurement of serum transaminases. See, for example, U.S. Pat. No. 4,241,179.

The reactions in both of these methods can be followed by a variety of techniques. See, for example, Henry et al (Eds.), Clinical Chemistry Principles and Technics, 2d Ed., Harper & Row, Publishers, pp. 873–892 (1974). NAD(H) can be measured either directly or after conversion of a redox indicator.

Alternatively, Deneke et al, U.S. Pat. No. 4,271,265, discloses a transaminase assay method in which the $\alpha$-ketoglutarate formed, as in reactions (1) or (2) above, is reacted with $\gamma$-aminobutyrate in the presence of $\gamma$-aminobutyrate transaminase with formation of succinate semialdehyde. Nicotine adenine dinucleotide phosphate (NADP) is reduced with the latter in the presence of succinate semialdehyde dehydrogenase to give NADPH (NADPH is reduced nicotine adenine dinucleotide phosphate), and the latter is measured either directly or after conversion with a tetrazolium salt and an electron carrier such as diaphorase, phenantroline methosulphate or phenazine methosulphate to a formazan dye.

All transaminases appear to share a common reaction mechanism and appear to have the same coenzyme or prosthetic group. This coenzyme is pyridoxal-5'-phosphate (PLP):

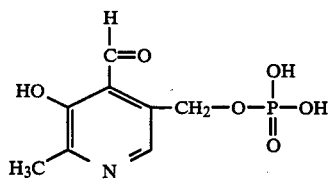

In transaminations PLP serves as the carrier for the $\alpha$-amino group to be transferred. The aldehyde group of the PLP-apoenzyme complex accepts an amino group from the donor amino acid, e.g. aspartate or alanine, forming a Schiff base. By oscillating between the aldehyde and amino forms, the PLP transfers the amino group from an amino acid to a keto acid. Serum transaminases require PLP for full catalytic activity, and a portion of such transaminases are present in serum in the apoenzyme form. Addition of PLP to compositions for the determination of such transaminases provides more complete activation and, thus, greater sensitivity. This was suggested in Hamfelt, *The Effect of Pyridoxal Phosphate on the Aminotransferase Assay in Blood,* Scand. J. Clin. Lab. Invest. 18 (Suppl. 99):181 (1966). The addition of PLP to transaminase assay reagents has been observed to cause a "positive drift" or incorrectly high reading in the 340 nanometer range. It has been suggested that incorporation of anions at high concentrations eliminates this shift. Sanderson J., Clin. Chem. 27:1035, Abs. 054 (1981).

SUMMARY OF THE INVENTION

Continuous flow analyzers using in-stream dialyzers occasionally permit unbound PLP to affect quantitative reading of protein-containing, e.g. serum, samples. PLP activation reagents have not been used on such analyzers because PLP is, in part, taken up by serum protein, such as albumin. As a result, unpredictable amounts of unbound PLP crossed the dialysis barrier.

In accordance with the present invention, it has been observed that the presence of certain amino-functionalized polymers negates the interfering effect of pyridoxal-5'-phosphate (PLP) on absorbance readings of liquids to be assayed. The amino groups of the amino-functionalized polymer irreversibly bind to PLP which is not bound to protein, thereby preventing its passage across the dialysis membrane. Further, the amino-functionalized polymer neither inhibits the transaminase activity nor removes PLP bound to the transaminase.

Thus, in accordance with the present invention, there is provided a composition for the determination of a transaminase in a liquid, which composition comprises a substrate for the transaminase, a reagent responsive to the reaction product of the transaminase and the substrate to provide a detectable response, pyridoxal-5'-phosphate and an amino-functionalized polymer. In a preferred embodiment, the reaction product-responsive reagent is an enzyme, for which the reaction product is a substrate, and a redox co-factor for the enzyme.

Further provided in accordance with the invention is a method for determining a transaminase in a liquid, which method comprises contacting said liquid with a composition which comprises a substrate for the transaminase, a reagent responsive to the reaction product of the transaminase and the substrate, pyridoxal-5'-phosphate and an amino-functionalized polymer, separating from said liquid any pyridoxal-5'-phosphate bound to amino-functionalized polymer, and, thereafter, observing any detectable response in said liquid.

DESCRIPTION OF THE PREFERRED EMBODIMENTS

Figure 1:
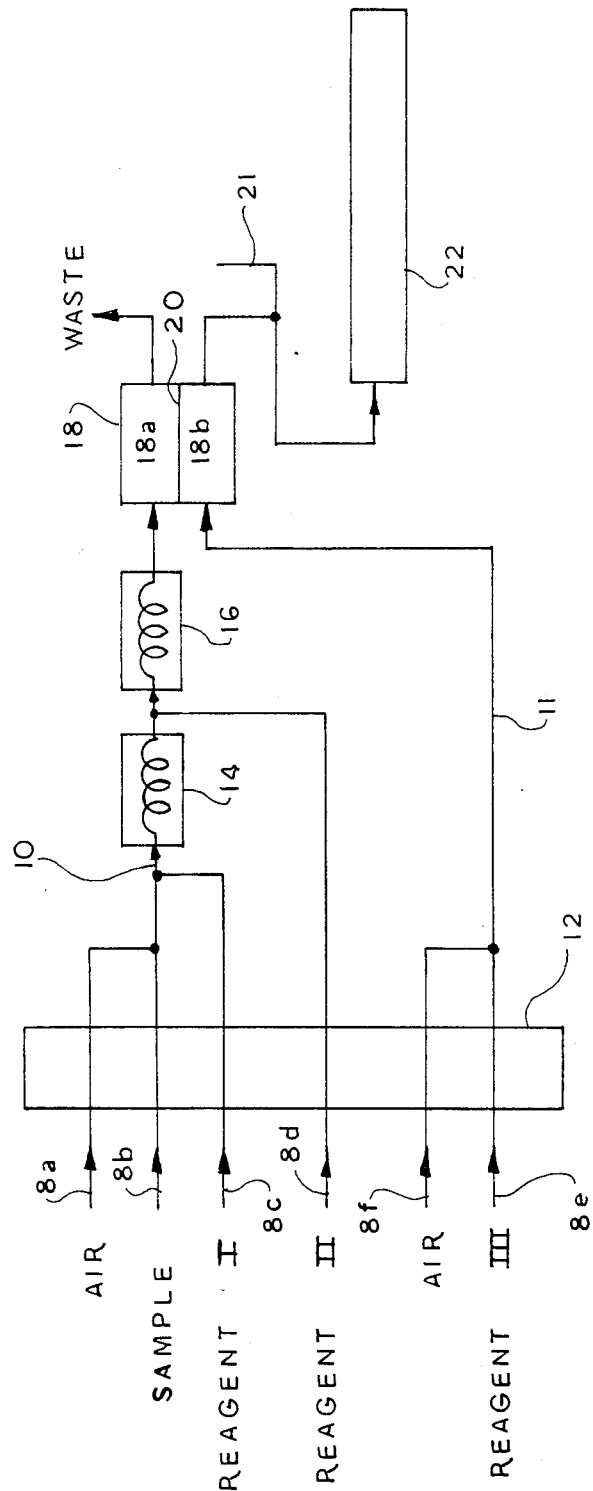
FIG. 1 is a schematic flow diagram of the continuous-flow analyzer having the modifications described and used in performing the experiments reported by Example 1.

Although specific terms are used in the following description for clarity, they refer only to the particular embodiment(s) selected for illustration, and are not intended to limit the scope of the invention.

Compositions in accordance with the invention are intended for use in the determination of transaminases, particularly in serum. As noted, the transaminases of primary clinical interest are glutamate oxalacetate transaminase (GOT) and glutamate pyruvate transaminase (GPT). The effect of interference associated with the use of pyridoxal-5'-phosphate activated reagents is avoided in accordance with the invention. One example of a composition for the determination of GOT is a reagent which includes a substrate comprising aspartate and α-ketoglutarate, an enzyme specific for the reaction product of the above substrate and GOT, which enzyme includes malate dehydrogenase and NAD, PLP and an amino-functionalized polymer. In a similar assay for the determination of GPT, the substrate comprises alanine and α-ketoglutarate and the enzyme specific for the reaction product of the substrate and GPT is lactate dehydrogenase and NAD. Glutamate dehydrogenase can be used in lieu of malate dehydrogenase or lactate dehydrogenase, respectively.

Other enzyme pathways are known which can be used for the determination of serum transaminases. For example, a composition for GOT determination can include a substrate comprising glutamate and oxalacetate, a reagent comprising α-aminobutyrate, γ-aminobutyrate transaminase, succinate semi-aldehyde dehydrogenase, and NADP, together with PLP and an amino-functionalized polymer. A comparable composition for the determination of GPT includes a substrate which comprises glutamate and pyruvate and a reagent which includes γ-aminobutyrate, γ-aminobutyrate transaminase succinate semi-aldehyde dehydrogenase and NADP.

As is known in the art, any of the above compositions can be made visually detectable by introduction of an appropriate redox indicator. Such indicators include o-dianisidine, o-toluidine, 3,3',5,5'-tetraalkylbenzidines, such as 3,3',5,5'-tetramethylbenzidine and coupled indicator systems. Such coupled indicator systems commonly comprise a hydrazone and a coupler such as trimethylaniline, 8-amino-1-naphthol-5,7-disulfonic acid or chromotropic acid.

In accordance with the invention, the above PLP-activated compositions are provided with an amino-functionalized polymer. Among these suitable for use are the amino-functionalized polymers having the formula:

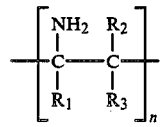

in which $R_1$ is hydrogen, alkyl, or aryl; $R_2$ and $R_3$ are independently hydrogen, hydroxyl, alkyl or aryl; and n is the number of repeating units of the polymer. Preferred are those polymers where $R_1$, $R_2$ and $R_3$ are each hydrogen. In another example, $R_1$ is methyl, ethyl or benzyl and $R_2$ and $R_3$ are hydrogen. In another example, $R_1$ and $R_3$ are both ethyl and $R_2$ is hydrogen. Another useful polymer is one in which one of $R_2$ or $R_3$ is hydroxyl and $R_1$ and the other of $R_2$ and $R_3$ are hydrogen. In yet another example, $R_2$ and $R_3$ are each methyl. Other examples within the scope of the above formula are contemplated as within the scope of the invention. Likewise preferred are those in which n is at least about 100. Polymeric molecules are contemplated where n is as high as about 1,000,000 or more. Particularly preferred is polyvinylamine.

When the compositions are used in solution form, the amino-functionalized polymer is preferably present in concentrations of from about 10 micromolar to about 40 micromolar. The pyridoxal-5'-phosphate is present in concentrations of from about 0.05 to about 0.2 millimolar. The concentrations of transaminase substrate, reagents responsive to the interaction of the transaminase and its substrate, and other reagents and constituents are present in concentrations known to be suitable for use with prior art assays.

The pyridoxal-5'-phosphate was obtained from Boehringer Mannheim Chemicals, Indianapolis, IN. The malate dehydrogenase/NADH and GOT/GPT diluent were obtained from Technicon Instruments Corporation, Tarrytown, NY. Pegosperse is a trademark for a series of polyglycol esters of fatty acids and was obtained from Glyco Chemicals, Inc., Greenwich, CT.

The activity of the enzyme preparations used in the examples is measured by the number of units of activity per milligram of dry weight. The Commission on Enzymes of the International Union of Biochemistry has defined an International Unit (IU) of enzyme activity as 1 micromole (μmol) of substrate utilized per minute under specified conditions of pH and temperature control.

EXAMPLE 1

In the experiments reported by this example, reagent compositions for the determination of GOT which contained a polyvinylamine, in accordance with the invention, were compared with a reagent composition which was identical except for the absence of the polyvinylamine and with a recognized standard method.

Method A, in accordance with the invention, made use of reagent compositions which were formulated as follows:

| Component | Quantity |
| --- | --- |
| Reagent I (per liter of distilled water): | |
| Tris(hydroxymethyl)aminomethane (Tris) | 20.1 grams (g) |
| Pyridoxal-5'-phosphate | 36.6 milligrams (mg) |
| L-aspartic acid | 77.0 g |
| Made to pH 7.8 with sodium hydroxide (NaOH) as needed. | |
| Reagent II (per liter of distilled water): | |
| Tris | 2.99 g |
| α-ketoglutarate disodium salt | 4.2 g |
| Polyvinylamine (22% w/v in H₂O) | 12.0 milliliters (ml) |
| Made to pH 8.7 with hydrochloric acid (HCl) as needed. | |
| Reagent III (per liter of distilled water): | |
| Porcine malate dehydrogenase (MDH) | 1,467 IU |
| NADH, disodium salt | 0.166 g |
| Ethylene diamine tetraacetic acid (EDTA), dipotassium salt | 0.037 g |
| Bovine Serum Albumin (BSA) | 0.49 g |
| Tris | 16.0 g |
| Made to pH 8.0 with HCl as needed. | |

For comparison, the same reagents except for the absence of polyvinylamine in Reagent II were used in an assay method, designated herein as Method B. Comparison was also made with the standard method recommended, for example, in Clinical Chemistry, 23:887–899 (1977) and 24:720–721, at 37° C., which is designated herein as Method C.

Methods A and B were performed using a continuous-flow analyzer of the type shown in FIG. 1. As illustrated, air, successive samples (separated by intrasample air segments) and Reagent I are introduced into the analyzer along pump tubes 8a, 8b and 8c, respectively, of peristaltic pump 12. The outlet of pump tubes 8a, 8b and 8c are connected to conduit 10, wherein the successive samples, segmented with intrasample air bubbles, are reacted with Reagent I. As each successive sample is treated identically, the treatment is described with respect to a single sample. The reacted sample is passed from conduit 10 and through incubator 14 where it is incubated for about 2.6 minutes at 37° C. The outlet of incubator 14 is connected to the inlet of a second incubator 16. Also, the outlet of pump tube 8d is connected to the inlet of incubator 16 and introduces Reagent II. A sample, now reacted with reagent II, is passed through incubator 16 and incubated for 3.0 minutes at 37° C. The fully reacted sample passes from incubator 16 to donor chamber 18a of dialyzer 18. Dialyzer 18 includes a recipient chamber 18b, which is separated from chamber 18a by a membrane 20 which is selectively permeable to small molecular weight compounds, so as to prevent passage of PLP bound to the amino-functionalized polymer into chamber 18b. Reagent III is introduced along pump 8e and combined with an air stream continuously introduced along pump tube 8f. The outlet of pump tubes 8e and 8f are connected to conduit 11. Accordingly, an air-segmented stream of Reagent III is passed from conduit 11 through chamber 18b as a recipient stream, so as to receive dialyzate to be analyzed. The outflow of chamber 18a is passed to waste, as indicated. The outflow of chamber 18b is passed to a spectrophotometer 22, whereat the absorbance is measured at 340 nanometers. Prior to passage of the reacted sample stream to spectrophotometer 22, the intrasample air bubbles and also a portion of the intersample air bubbles in the continuous stream outletted from chamber 18b are debubbled, in conventional fashion, by debubbler 21.

Method C was performed on a Gilford 260 analyzer obtained from Gilford of Oberlin, OH.

A series of 20 randomly selected human serum samples were assayed by all three methods with the results reported as GOT activity, expressed as International Units/Liter (IU/L) in Table I.

TABLE I

| Sample | Method A | Method B | Method C |
| --- | --- | --- | --- |
| 1 | 37 | 48 | 33 |
| 2 | 28 | 40 | 35 |
| 3 | 26 | 40 | 28 |
| 4 | 43 | 56 | 45 |
| 5 | 33 | 45 | 33 |
| 6 | 26 | 37 | 26 |
| 7 | 23 | 35 | 26 |
| 8 | 23 | 35 | 25 |
| 9 | 50 | 60 | 47 |
| 10 | 41 | 51 | 40 |
| 11 | 91 | 104 | 89 |
| 12 | 79 | 89 | 67 |
| 13 | 137 | 151 | 146 |
| 14 | 96 | 105 | 100 |
| 15 | 101 | 115 | 98 |
| 16 | 37 | 45 | 35 |
| 17 | 93 | 101 | 110 |
| 18 | 91 | 99 | 108 |
| 19 | 71 | 81 | 69 |
| 20 | 184 | 185 | 201 |

As may be seen from these data, Method A of the invention correlates closer to reference Method C than does Method B.

EXAMPLE 2

In the experiments reported by this example, various amounts of polyvinylamine (PVA) were evaluated to determine that amount required to remove interference due to predetermined amounts of pyridoxal-5'-phosphate.

This quantitative evaluation compared compositions in accordance with the invention which were formulated as follows:

| Component | Quantity |
| --- | --- |
| Reagent I (per liter distilled water): | |
| Tris(hydroxymethyl)aminomethane (Tris) | 9.5 g |
| Tris HCl | 5.5 g |
| Pyridoxal-5'-phosphate (PLP) | 62 mg |
| L-aspartic acid, sodium salt | 54.5 g |
| Made to pH 8.0 with NaOH or HCl as needed. | |
| Reagent II (per liter distilled water): | |
| α-ketoglutarate, disodium salt | 14.5 g |
| Tris | 8.0 g |
| Made to pH 8.7 with HCl as needed. | |

| Reagent III | A | B | C | D | E | F | G | H |
| --- | --- | --- | --- | --- | --- | --- | --- | --- |
| PVA (10% w/v H₂O | 0 | .05 ml | .100 ml | .250 ml | .500 ml | .750 ml | 1.00 ml | 1.25 ml |
| H₂O | 2.5 | 2,45 | 2.40 | 2.25 | 2.0 | 1.75 | 1.50 | 1.25 |

| -continued | | | | | | | |
|---|---|---|---|---|---|---|---|
| ml | ml | ml | ml | ml | ml | ml | ml |

The above solutions were used in testing aliquots of human serum taken from a sample preparation designated as R4 and containing 10 ml of pooled human serum mixed with 1.5 ml of Pegosperse ™.

The assay was conducted by incubating, for four minutes at 37° C. the following volumes of each of the above solutions:

| Solution | Volume (ml) |
|---|---|
| $R_1$ | 3.0 |
| $R_2$ | 0.7 |
| $R_3$ | 2.5 |
| $R_4$ | 1.0 |

Absorbance of each solution was measured at 410 nanometers on a Gilford 260 spectrophotometer to quantitate the amount of irreversible binding of pyridoxal-5'-phosphate by polyvinylamine.

Figure 2:
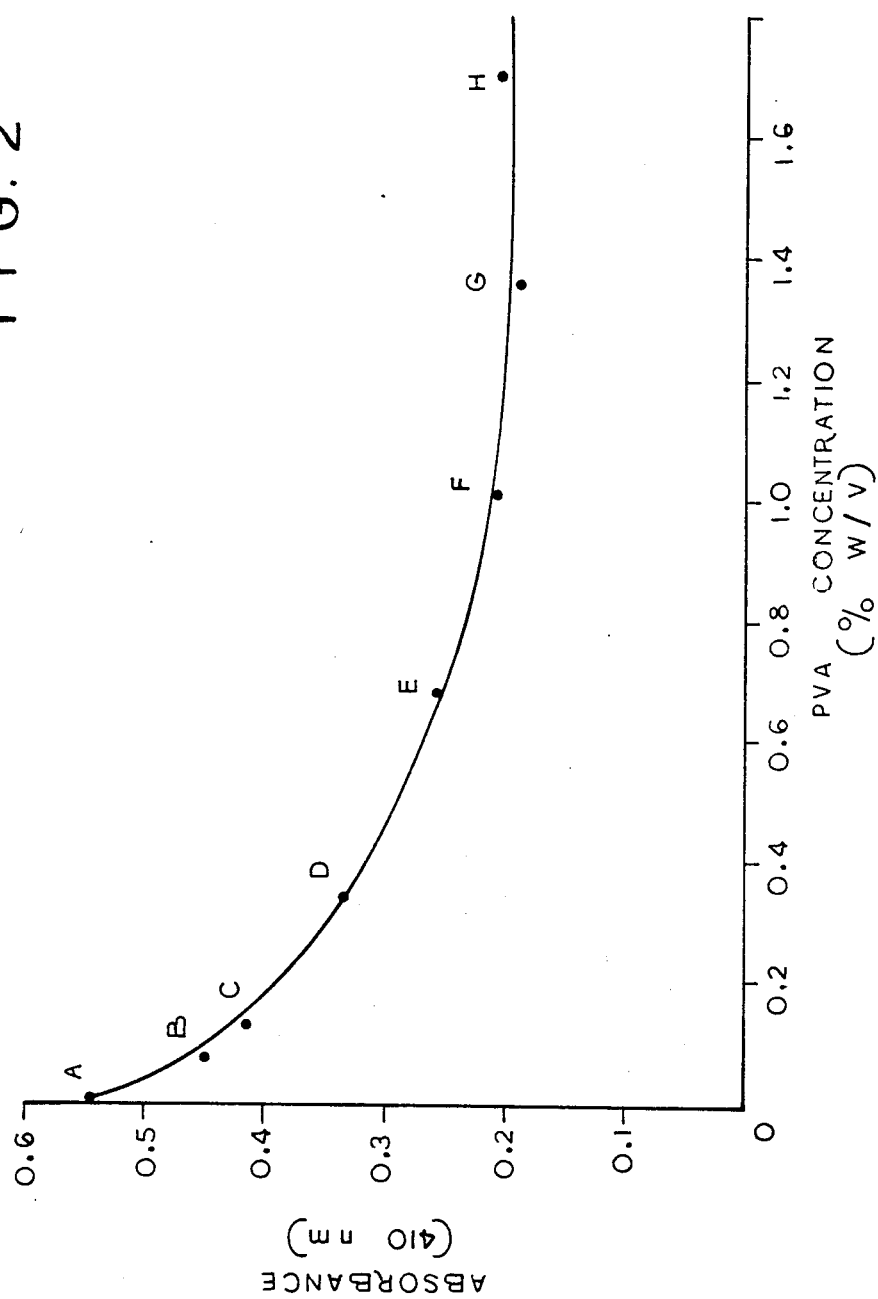
FIG. 2 is a graphical representation of the data obtained in accordance with Example 2.

The results which were obtained are graphically illustrated in FIG. 2, which shows that for solutions with at least 1% w/v PVA, such as those in which $R_3$ formulations F, G and H are used, all 410 nanometer absorbance due to that of PLP is eliminated. That small amount of residual absorbance which is also observed is due to α-ketoglutarate present in the liquid under analysis.

Although the invention has been described with particularity, numerous changes in the details can be resorted to without departing from the scope of the invention.

What is claimed is:

1. A composition for the determination of a transaminase in a sample, which composition comprises:
   (a) a substrate for said transaminase;
   (b) a reagent responsive to the reaction product of said transaminase and said substrate to provide a detectable response;
   (c) pyridoxal-5'-phosphate; and
   (d) an amino functionalized polymer having the formula

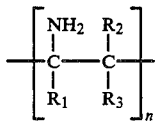

wherein $R_1$ is hydrogen, alkyl or aryl; $R_2$ and $R_3$ are independently hydrogen, alkyl or aryl; and n is the number of repeating units of the polymer in an amount sufficient to remove the signal interference caused by pyridoxal-5'-phosphate.

2. The composition of claim 1 wherein the reagent of (b) comprises an enzyme for which the reaction product is a substrate and a redox co-factor for the enzyme.

3. The composition of claim 2 wherein the transaminase is glutamate oxalacetate transaminase, the substrate comprises aspartate and α-ketoglutarate, the enzyme specific for the reaction product comprises malate dehydrogenase and the redox coenzyme is nicotine adenine dinucleotide.

4. The composition of claim 2 wherein the transaminase is glutamate pyruvate transaminase, the substrate comprises alanine and α-ketoglutarate, the enzyme specific for the reaction product is lactate dehydrogenase and the redox coenzyme is nicotine adenine dinucleotide.

5. The composition of claim 2 wherein the enzyme specific for the reaction product comprises glutamate dehydrogenase.

6. The composition of claim 1 wherein the transaminase is glutamate oxalacetate transaminase, the substrate comprises glutamate and oxalacetate, the reagent responsive to the reaction product comprises γ-aminobutyrate, γ-aminobutyrate transaminase, succinate semialdehyde dehydrogenase and nicotine adenine dinucleotide phosphate.

7. The composition of claim 1 wherein the transaminase is glutamate pyruvate transaminase, the substrate comprises glutamate and pyruvate, the reagent responsive to the reaction product comprises γ-aminobutyrate, γ-aminobutyrate transaminase, succinate semialdehyde dehydrogenase and nicotine adenine dinucleotide phosphate.

8. The composition of any of claims 1-7 which further comprises a redox indicator.

9. The composition of claim 1 wherein $R_1$, $R_2$ and $R_3$ are each hydrogen.

10. The composition of claim 1 wherein $R_1$, $R_2$ and $R_3$ are each hydrogen and n is at least about 100.

11. The composition of claim 1 wherein $R_1$ is methyl, ethyl or benzyl and $R_2$ and $R_3$ are hydrogen.

12. The composition of claim 1 wherein $R_1$ and $R_3$ are both ethyl and $R_2$ is hydrogen.

13. The composition of claim 1 wherein one of $R_2$ and $R_3$ is hydroxyl and $R_1$ and the other of $R_2$ and $R_3$ is hydrogen.

14. The composition of claim 1 wherein $R_1$ is hydrogen and both of $R_2$ and $R_3$ are methyl.

15. A method for determining a transaminase in a liquid, which method comprises
   contacting said liquid with a composition which comprises a substrate for the transaminase, a reagent responsive to the reaction product of the transaminase and the substrate, and pyridoxal-5'-phosphate to form a reaction mixture;
   thereafter, contacting said reaction mixture with an amino-functionalized polymer;
   separating from said liquid any pyridoxal-5'-phosphate bound to amino-functionalized polymer; and, thereafter,
   observing any detectable response in said liquid.

* * * * *